United States Patent
Blattner et al.

(12) 
(10) Patent No.: US 11,174,284 B2
(45) Date of Patent: Nov. 16, 2021

(54) PURIFICATION OF CRM 197 FROM BACTERIA

(71) Applicant: SCARAB GENOMICS, LLC, Madison, WI (US)

(72) Inventors: Frederick R. Blattner, Madison, WI (US); David Frisch, Fitchburg, WI (US); Charles Landry, Fitchburg, WI (US); John Brandon, Madison, WI (US)

(73) Assignee: SCARAB GENOMICS, LLC, Madison, WI (US)

( * ) Notice: Subject to any disclaimer, the term of this patent is extended or adjusted under 35 U.S.C. 154(b) by 0 days.

(21) Appl. No.: 16/500,812

(22) PCT Filed: Apr. 3, 2018

(86) PCT No.: PCT/US2018/025969
§ 371 (c)(1),
(2) Date: Oct. 3, 2019

(87) PCT Pub. No.: WO2018/187388
PCT Pub. Date: Oct. 11, 2018

(65) Prior Publication Data
US 2020/0207804 A1    Jul. 2, 2020

Related U.S. Application Data

(60) Provisional application No. 62/481,534, filed on Apr. 4, 2017.

(51) Int. Cl.
| | | |
|---|---|---|
| *C07K 1/16* | (2006.01) | |
| *C07K 1/18* | (2006.01) | |
| *C07K 14/34* | (2006.01) | |
| *B01D 15/18* | (2006.01) | |
| *B01D 15/32* | (2006.01) | |
| *B01D 15/36* | (2006.01) | |
| *B01D 15/38* | (2006.01) | |

(52) U.S. Cl.
CPC .......... *C07K 1/165* (2013.01); *B01D 15/1871* (2013.01); *B01D 15/327* (2013.01); *B01D 15/362* (2013.01); *B01D 15/363* (2013.01); *B01D 15/3847* (2013.01); *C07K 1/18* (2013.01); *C07K 14/34* (2013.01)

(58) Field of Classification Search
None
See application file for complete search history.

(56) References Cited

U.S. PATENT DOCUMENTS

| | | | |
|---|---|---|---|
| 8,802,448 B2 * | 8/2014 | Ait-Haddou | B01D 15/3847 436/532 |
| 2013/0079498 A1 * | 3/2013 | Gilljam | C12N 9/6424 530/381 |
| 2013/0202626 A1 * | 8/2013 | Linke | B01D 15/166 424/183.1 |
| 2014/0193876 A1 * | 7/2014 | Goerke | C12N 9/1077 435/193 |

FOREIGN PATENT DOCUMENTS

| | | | | |
|---|---|---|---|---|
| WO | WO-2015200645 A1 * | 12/2015 | | B01D 15/361 |

OTHER PUBLICATIONS

Moghadam et al. Rep Biochem Mol Biol Oct. 2015; 4(1):19-24 (Year: 2015).*
Holmes et al. The Journal of Infectious Diseases, 2000; 181 (Suppl 1) 1:S156-67 (Year: 2000).*
Hirano et al. Journal of Chromatography A, 1338 (2014) 58-66 (Year: 2014).*

* cited by examiner

*Primary Examiner* — Oluwatosin A Ogunbiyi
(74) *Attorney, Agent, or Firm* — Christopher M. Cabral; Much Shelist, PC

(57) ABSTRACT

The present invention relates to the use of redox agents for purification of the CRM 197 variant of diphtheria toxin. The invention further relates to multi-step purification of CRM 197 from bacterial fermentates.

16 Claims, 8 Drawing Sheets

PURIFICATION OF CRM 197 FROM BACTERIA

CROSS-REFERENCE TO RELATED APPLICATIONS

This application is a national stage application (under 35 U.S.C. § 371) of PCT/US2018/025969, filed Apr. 3, 2018, which claims the benefit of U.S. Provisional Patent Application Ser. No. 62/481,534, filed Apr. 4, 2017, the full disclosures of which are incorporated herein by reference.

FIELD OF THE INVENTION

The present invention is directed to the purification of recombinant CRM 197 from bacterial production organisms.

BACKGROUND OF THE INVENTION

Diphtheria toxin (DTx) is a two-component exotoxin of *Corynebacterium diphtheriae* synthesized as a single polypeptide chain of 535 amino acids containing an A (active) domain and a B (binding) domain linked together by a disulfide bridge. The toxin binds to a cell receptor (HB-EGF receptor) and enters the cell by endocytosis where the A domain is released from the B domain by proteolytic cleavage. The A domain then exits the endosome through pores made by the B domain and enters the cytoplasm where it inhibits protein synthesis by ADP-ribosylation of host elongation factor 2, ultimately resulting in cell death.

CRM 197 is a mutated form of Dtx containing a single amino acid substitution of glutamic acid for glycine (G52E) that renders the protein enzymatically inactive and non-toxic. CRM 197 has been found to be an ideal carrier for conjugate vaccines against encapsulated bacteria. Conjugate vaccines comprise CRM 197 covalently linked to poorly immunogenic and T-cell independent capsular polysaccharides, thus creating conjugate antigens that are highly immunogenic and result in long-lasting immunity against the antigen(s).

Vaccines containing CRM 197 as a carrier protein have been successfully used to immunize millions of children and include Menveo®, a tetravalent conjugate vaccine against serogroups A-C-W135-Y of *Neisseria meningitidis*, Menjugate® and Meningitec® (against serotype C of *N. meningitidis*), Vaxem-Hib® and HibTITER® (against *Haemophilus influenzae* type B, Hib), and the multivalent pneumococcal conjugate Prevnar™.

In contrast to tetanus and diphtheria toxins, CRM 197 does not require chemical detoxification and can therefore be purified to homogeneity and used directly for conjugation. CRM 197 is currently manufactured by the fermentation of either *Corynebacterium diphtheriae* C7, where it is expressed from multiple lysogens of the endogenous β phage. The yield of CRM 197 (which is released into the media during *C. diphtheriae* fermentation) is low, ranging from tens of mg/L to about 200 mg/L and requires use of biosafety level 2 facilities, resulting in a retail price of about US $500 per milligram of CRM 197. A single dose of vaccine typically contains about 10 to 60 micrograms of CRM 197 and over 150 million doses are used each year. Current demand for conjugate CRM 197 vaccines has outpaced supply and has resulted in delays in initiating vaccination programs in developing countries placing the health of millions of children at risk.

More recently, alternative schemes for producing CRM 197 from recombinant bacteria have been developed. Generally, these schemes rely on use of recombinant *Pseudomonas flurorescens* or *Escherichia coli* strains to produce CRM 197. For example, WO 2015/134402 discloses a process for producing recombinant CRM 197 in a reduced genome *E. coli* host to increase production of CRM 197. WO 2016/079755 discloses use of codon optimized variants of the gene encoding CRM 197 to improve yields of CRM 197 from *E. coli* host strains. WO 2012/173876 and WO 2015/117093 each disclose schemes for purifying DTx and CRM 197 from *E. coli* host strains.

A major factor contributing to the high price and short supply of CRM 197 is the difficulty in preparing high amounts of properly-folded un-degraded CRM 197. Recombinant systems for producing CRM 197 generally produce insoluble aggregates or inclusion bodies, which require complicated and inefficient methods for purifying the inclusion bodies, solubilizing the protein in vitro, followed by a series of steps designed to properly re-nature the protein into its native conformation before the protein can be used. Alternatively, recombinant expression systems rely on heterologous transport systems to translocate the protein in to the periplasmic space from which it can be recovered.

Use of heterologous leader sequences which are cleaved upon translocation of the protein across the membrane produces a CRM 197 product that lacks the N-terminal methionine. Equally importantly, translocation of CRM 197 into the periplasm allows di-sulfide bridges between the cysteine (Cys) residues 186 and 201, and 461 and 471 to form. Such di-sulfide bridges cannot be established within the highly reducing environment of the bacterial cytoplasm, but are possible in the oxidative environment of the periplasm. Unfortunately, the redox state of periplasmic proteins is altered significantly during cell lysis and protein purification. We report here that maintaining the proper di-sulfide bridges through the course of purification of CRM 197 improves the stability and reduces subsequent degradation of CRM 197 and thus, represents a significant advance in the art.

SUMMARY OF THE INVENTION

The present invention relates to a method for purifying CRM 197 protein from bacterial fermentate. In preferred embodiments, an oxidized di-sulfide compound is added to reduce degradation of CRM 197 and maintain solubility of the protein. Typical protein purification methods are insufficient for recovering intact CRM 197 from bacterial lysates with high purity. Such methods are compromised by the inability to discriminate intact CRM 197 from its most common proteolytic products. This is especially a problem at the highly labile cleavage position between the A and B domains of the protein. The disulfide bridge between Cys-186 and Cys-201 connects the two domains even if the amino acid backbone is cleaved at amino acid positions 190, 192, and 193. The inventors have discovered that establishing and preserving this disulfide bridge protects the protein from cleavage at or near these positions during isolation and purification of CRM 197 (FIG. 1). Current methods for purifying CRM 197 lack any system for mitigating redox changes. The use of redox agents as disclosed in the present invention improves the yield of intact CRM 197 even beyond the yield of intact CRM 197 obtained in the presence of protease inhibitors. By maintaining the proper redox state of the intramolecular disulfide bonds within CRM 197 through the course of purification, intact CRM 197 is recovered at high levels with significantly reduced incidence of contaminating proteolysis products relative to CRM 197 produced by other means (FIG. 2). Several novel and improved purification schemes for CRM 197 are also disclosed.

DETAILED DESCRIPTION OF THE INVENTION

Figure 1:
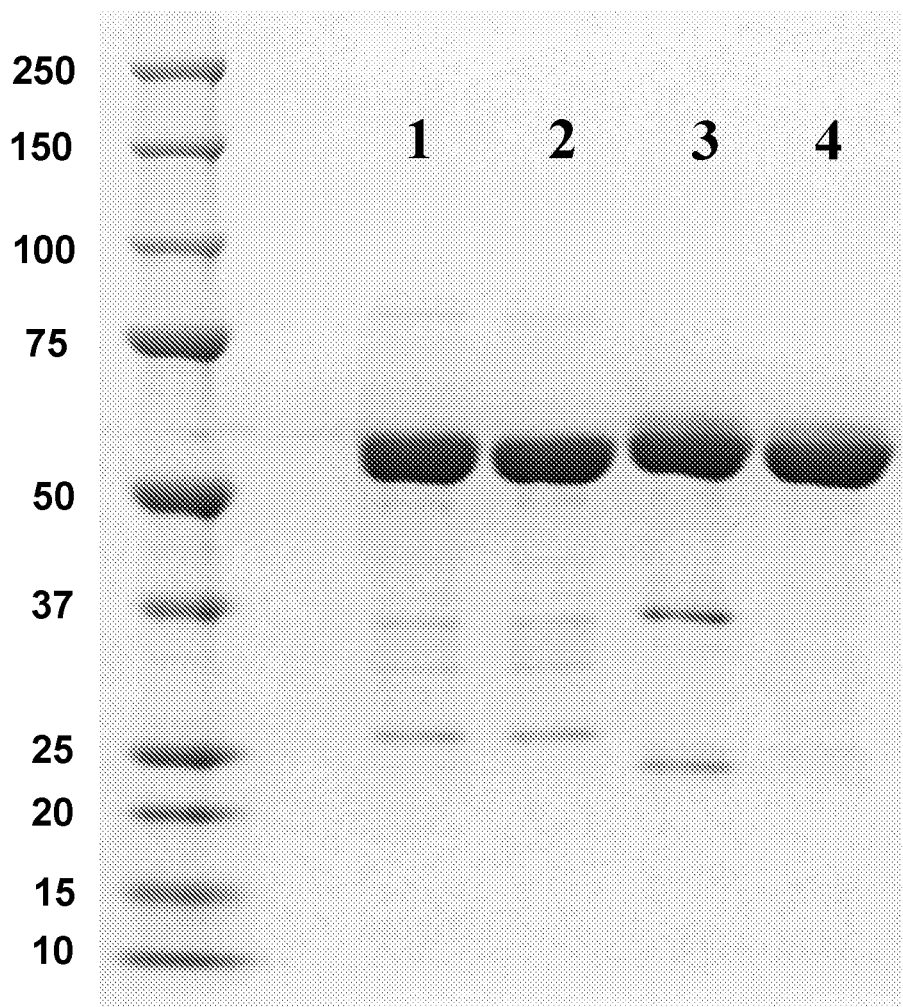
FIG. 1 demonstrates the effect of a redox agent on the stability of CRM 197 produced by the present invention. Two CRM 197 preparations were generated, one with 1 mM glutathione disulfide as redox agent (lanes 2 and 4) and one without addition of any redox agent (lanes 1 and 3). Aliquots of 2 micrograms of each CRM 197 preparation were either treated with DTT (lanes 3 and 4) or untreated (lanes 1 and 2) prior to analysis by denaturing PAGE analysis on a NuPAGE® bis Tris 4-12% gradient SDS polyaccrylamide gel (Invitrogen, Thermo Fisher Scientific, Waltham Mass.). Addition of DTT to the samples ensures complete reduction of disulfide bridges in the protein preparation to allow separation of any proteolysis degradation products. The result of proteolysis is evident as bands of approximately 37 kD and 21 kD as seen in lane 3. The gel includes Precision Plus Protein™ size markers (Biorad, Hercules Calif.).

While the present invention is capable of being embodied in various forms, the description below of several embodiments is made with the understanding that the present disclosure is to be considered as an exemplification of the invention, and is not intended to limit the invention to the specific embodiments illustrated. Headings are provided for convenience only and are not to be construed to limit the invention in any manner Embodiments illustrated under any heading may be combined with embodiments illustrated under any other heading.

The use of numerical values in the various ranges specified in this application, unless expressly indicated otherwise, are stated as approximations as though the minimum and maximum values within the stated ranges were both preceded by the word "about." In this manner, slight variations above and below the stated ranges can be used to achieve substantially the same results as values within the ranges. As used herein, the terms "about" and "approximately" when referring to a numerical value shall have their plain and ordinary meanings to one skilled in the pertinent art at issue. Also, the disclosure of ranges is intended as a continuous range including every value between the minimum and maximum values recited as well as any ranges that can be formed by such values. This includes ranges that can be formed that do or do not include a finite upper and/or lower boundary. This also includes ratios that are derivable by dividing a given disclosed numeral into another disclosed numeral. Accordingly, the skilled person will appreciate that many such ratios, ranges, and ranges of ratios can be unambiguously derived from the data and numbers presented herein and all represent various embodiments of the present invention.

As used herein, the term "bacterial cell lysate" means the product of complete or partial lysis of a bacterial cell. Typically, a bacterial cell lysate contains proteins, nucleic acids, cell wall and cell membrane fragments, and is generally quite viscous. Common methods of lysing bacterial cells are well known to those of ordinary skill in the art and include, without limitation osmotic shock, use of detergents, use of specific cell wall degrading agents such as lysozyme, pressure changes, high sheer forces, and bacteriophage induced lysis. Partial cell lysis can be achieved by removal of the outer membrane of gram-negative bacteria to provide a lysate enriched for the components of the periplasm. For example, the PeriPrep kit marketed by EpiCentre (Madison, Wis.) relies on a combination of lysozyme and a buffer with sufficient osmolality to stabilize the bacterial protoplast, thus allowing recovery of periplasmic contents while minimizing contamination from cytoplasmic proteins. Of particular interest to the current invention is use of the microfluidizer to lyse bacterial cells by exposing them to extremely high sheer forces generated by forcing the cells through a series of microchannels at high pressure. One advantage of microfluidizer technology is that it easily scales from sub-milliliter to multi-thousand liter scale, which makes it particularly useful in large scale preparation of difficult to express proteins such as CRM 197.

The term "CRM 197" used herein refers to cross-reacting material 197, a diphtheria toxin variant having a single G-A transition leading to the substitution of glycine (at position 52 in the wild-type toxin) with glutamic acid in CRM 197. This missense mutation is responsible for the loss of ADP-ribosyltransferase activity. See Giannini, et al., Nucleic Acids Res. 12(10):4063-4069 (1984) and Malito, et al., Proc. Natl. Acad. Sci. U.S.A. 109(14):5229-5234 (2014). As used herein, "CRM 197" explicitly refers to the intact protein itself and excludes the domains produced by proteolysis, which are explicitly referred to as "domains" to differentiate from the intact "CR 197." CRM 197 has an estimated isoelectric point of 5.85. The "isoelectric point" refers to the pH at which a polypeptide's positive charge balances its negative charge. Isoelectric point can be calculated from the net charge of the amino acid residues of the polypeptide or can be determined by isoelectric focusing. The term "recombinant bacterium" means a bacterium modified to improve its fermentation performance Such improvements include, but are not limited to increased expression of native or heterologous proteins, nucleic acids or small molecules. Typically, recombinant bacteria are transformed with plasmids that have been constructed using genetic engineering techniques although direct modification of the bacterial chromosome is also contemplated. Of particular relevance concerning purification of CRM 197 are recombinant strains of *E. coli*, such as *E. coli* K-12 derivatives such as MG1655, JM109, DH10b, and DH5alpha. Other *E. coli* strains, such as the *E. coli* B strain derivative BL21/DE3 are also commonly used to produce heterologous proteins such CRM 197. Recombinant *Pseudomonas* sp. such as the proprietary Pfenex *Pseudomonas* strain. *P. fluorescens, P. aerugenosa*, and *P. putida* are also suitable for production of CRM 197 by the methods of the invention.

The term "redox agent" means any substance that can affect the oxidation state of a molecule. With respect to purification of CRM 197, the four cysteine residues that form disulfide bridges among themselves do so only in the fully oxidized state. Under fully reduced conditions neither the disulfide bridge between Cys 186 and Cys 201, nor Cys 461 and Cys 471 can form. Under partial reducing conditions one or another of the disulfide bridges may form. Redox agents particularly suited to maintaining this state includes those containing a disulfide bridge similar to those found in CRM 197. Such disulfide bridge redox agents include, but are not limited to glutathione disulfide, cystine, cystamine, diphenyl disulfide, and lipoic acid. Certain organic and inorganic salts are also suited for use as redox agents within the scope of the present invention. Such organic and inorganic salts redox agents include, but are not limited to sodium iodate, 1,10 phenanthroline, $CuCl_2$, and $FeSO_4$. Addition of either kind redox agent may serve to titrate the activity of any residual reduction potential within the original bacterial cell lysate or mitigate the reductive potential of reductive environments encountered in the course of CRM 197 purification.

The term "separation agent" means any substance capable of interaction with constituents of the CRM 197 containing mixture. Typically a separation agent refers to a chromatographic substrate, including but not limited to, hydrophobic interaction resins, anion exchange resins, cation exchange resins, and hydroxyapatite. Such separation agents can be used in column chromatography or in batch separation modes.

The term "solubilizing agent" means any substance that makes a substance more soluble, especially in water. Such agents can be detergents or compounds with detergent like properties. Of special interest to the present invention are solubilizing agents that cause little or no protein denaturation. Agents of particular interest are urea, cyclodextrins, short chain fatty acid detergents, and basic amino acids.

The term "b number" used herein refers to the unique ID assigned to each gene of the K-12 MG1.655 strain as described in Blattner et al., Science 277:1453-1474 (1997).

By "purifying" a polypeptide (e.g. CRM 197) from a composition comprising the polypeptide and one or more contaminants is meant increasing the degree of purity of the polypeptide in the composition by removing (completely or partially) at least one contaminant from the composition. A "purification step" may be part of an overall purification process resulting in a "homogenous" composition. "Homogenous" is used herein to refer to a composition comprising at least about 70% by weight of the polypeptide (e.g. CRM 197), based on total weight of the composition, preferably at least about 80% by weight, more preferably at least about 90% by weight, even more preferably at least about 95% by weight.

The term "flow-through mode" as used herein denotes an operation mode of a chromatography method (e.g. anion exchange chromatography) in which a solution comprising a polypeptide of interest (e.g. CRM 197) is brought in contact with a stationary solid phase whereby the substance of interest does not bind to that stationary phase and as a result the polypeptide of interest is obtained in the flow-through, whereas impurities also present in the solution bind to the stationary phase and are removed from the solution.

The term "bind/elute mode" or "bind and elute mode" as used herein denotes an operation mode of chromatography method in which a solution containing a polypeptide of interest is brought in contact with a stationary solid phase, whereby the polypeptide of interest binds to the stationary phase and as a result, the polypeptide of interest is retained on the stationary phase whereas impurities are removed with the flow-through or are resolved from the polypeptide of interest upon elution of the stationary phase.

The term "hydroxyapatite chromatography" or "HAC" as used herein denotes a chromatography method that employs a certain form of calcium phosphate as chromatography material. Any hydroxyapatite resin may be used to carry out purification of CRM 197 according to the methods described herein. In a preferred embodiment, it is carried out on a ceramic hydroxyapatite resin, such as a type I or type II hydroxyapatite resin. The hydroxyapatite resin may have particles of any size such as 20, 40 or 80 μm or any size there between. In a preferred embodiment, the ceramic hydroxyapatite resin comprises particles having a size of about 39 μm or 40 μm. A hydroxyapatite resin that is particularly suitable is a column commercially available under the name Ca++ Pure-HA. (Tosoh Bioscience). Other exemplary hydroxyapatite resins include, without limitation, Bio-Gel HT, Bio-Gel HTP, Macro-Prep Ceramic (Biorad Laboratories), Hydroxyapatite Type 1, Type II, HA Ultrogel (Sigma Aldrich Chemical Corp., USA), Hydroxyapatite Fast Flow and High Resolution (Calbiochem).

The term "anion exchange chromatography" or "AIEX" as used herein denotes a chromatography process that relies on charge-charge interactions between the proteins in the sample and the charges immobilized on the resin. In anion exchange chromatography, the binding ions of the protein are negative, and the functional group immobilized on the resin is positive. Commonly used anion exchange resins are Q-resin, a quaternary amine, and DEA resin. (DiEthylAminoEthane). However, any anion exchange chromatography resin may be used to carry out purification of CRM 197 according, to the methods described herein. The anion exchange chromatography resin is preferably a strong anion exchange anion exchange resin having —N$^+$(CH$_3$)$_3$ functional groups or a resin having similar characteristics. Typical strong anion exchange resins for use in the methods described herein comprise functional groups such as quaternary aminoethyl (QAE) moieties, quaternary ammonium (Q) moieties and trimethylammoniumethyl (TMAE) groups. An anion exchange resin that is particularly suitable for use in the methods herein described is Tosoh GigaCap Q 650M (Tosoh Bioscience, Germany).

The term "hydrophobic interaction chromatography" or "HIC" denote a chromatography method in which a hydrophobic interaction chromatography material is employed. A "hydrophobic interaction chromatography material" is a chromatography material to which hydrophobic groups, such as butyl-, octyl-, or phenyl-groups, are bound as chromatographic functional groups. A polypeptide of interest (e.g. CRM 19) is separated depending on the hydrophobicity of its surface exposed amino acid side chains which can interact with the hydrophobic groups of the hydrophobic interaction chromatography material. The interactions between polypeptide of interest and the chromatography material can be influenced by e.g. temperature, solvent and ionic strength of the solvent. A temperature increase e.g. supports interaction between the polypeptide and the hydrophobic interaction chromatography material as the motion of the amino acid side chains increases and hydrophobic amino acid side chains buried inside the polypeptide at lower temperatures become accessible. Any hydrophobic interaction chromatography material may be used in HIC according to the methods herein described, although a resin having hydrophobic groups (e.g. polypropylene glycol) with a relatively low hydrophobicity is preferred. A hydrophobic interaction chromatography resin that is particularly suitable for purification of CRM 197 according to the methods described herein is a Tosoh PPG 600M (Tosoh Bioscience, Germany).

The term "mixed-mode chromatography" or "mixed mode chromatography" used herein denote a chromatography method in which a chromatography material is used comprising a ligand (or ligands) containing a charged moiety (preferably a negatively charged moiety) and a hydrophobic moiety (preferably comprising a phenyl group, optionally a substituted phenyl moiety such as benzoic acid) wherein the charged moiety preferably has cation exchange properties and the hydrophobic moiety has hydrophobic interaction chromatography properties. Cation exchange/ HIC mixed mode chromatography separates a protein of interest (e.g. CRM 197) on the basis of both electrostatic and hydrophobic interactions. A mixed-mode chromatography resin that is particularly suitable for purification of CRM 197 according to the methods described herein is CMM Hyper-Cel resin (Pall Corporation) which comprises a ligand containing a phenyl moiety substituted with a carboxylic acid and a primary amine, conferring both cation exchange and hydrophobicity properties to the resin, as shown below.

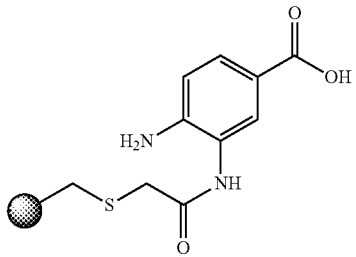 [SMILES: CCSCC(=O)Nc1cc(C(=O)O)ccc1N]

In preferred embodiments, the mixed-mode chromatography resin comprises a ligand comprising an aromatic or heteroaromatic moiety, preferably phenyl, substituted with a primary amine, and preferably further substituted with a carboxylic acid, such as those described at columns 19-38 of U.S. Pat. No. 8,802,448, the entire contents of which are hereby incorporated by reference.

The term "excipient" as used herein refers to an inert substance which is commonly used as a diluent, vehicle, preservative, binder or stabilizing agent for drugs which imparts a beneficial physical property to a formulation, such as increased protein stability, increased protein solubility, and/or decreased viscosity. Examples of excipients include, but are not limited to, proteins (e.g., serum albumin), amino acids (e.g., aspartic acid, glutamic acid, lysine, arginine, glycine), surfactants (e.g., SDS, TWEEN (polysorbate) 20, TWEEN (polysorbate) 80, poloxamers, polysorbate and nonionic surfactants), saccharides (e.g., glucose, sucrose, lactose, maltose and trehalose), polyols (e.g., mannitol and sorbitol), fatty acids and phospholipids (e.g., alkyl sulfonates and caprylate). For additional information regarding excipients, see Remington's Pharmaceutical Sciences (by Joseph P. Remington, 18th ed., Mack Publishing Co., Easton, Pa.), which is incorporated herein in its entirety.

In an embodiment of the invention CRM 197 is produced by a recombinant bacterium. The CRM 197 may be expressed from an inducible or constitutive promoter. The CRM 197 may be translocated to the periplasm of the recombinant bacterium by a variety of routes. Alternatively, the CRM 197 may remain within the cytosol of the recombinant bacterium. A bacterial fermentate containing the recombinant bacteria expressing CRM 197 is obtained. The bacterial fermentate may be directly recovered from the fermenter or it may be recovered from a frozen stock by gentle thawing. To the fresh or thawed frozen bacterial fermentate an equal volume of solubilizing agent is added. The solubilizing agent may be a basic amino acid, such as arginine, lysine ornithine, or proline. In a preferred embodiment an equal volume of 500 mM to 1 M L-arginine, preferably about 750 mM L-arginine pH 8.0 is added to the bacterial fermentate. The mixture is thoroughly blended and then a redox agent is added, preferably to a final concentration of about 0.3 mM to about 1.5 mM, more preferably to a final concentration of about 1 mM. Preferably, the redox agent contains an oxidized disulfide moiety (i.e., is a thiol-based redox agent). In a preferred embodiment the redox agent is glutathione disulfide (oxidized dimer of L-glutathione) added to a final concentration of about 1 mM. In another preferred embodiment the redox agent is cystine (oxidized dimer of cysteine) added to a final concentration of about 1 mM. The bacterial cells within the oxidized mixture are then lysed to release CRM 197. In a preferred embodiment cell lysis is achieved by passing the oxidized bacterial fermentate through a microfluidizer or other mechanical disruptor. Other cell lysis methods such as sonication or enzymatic or chemical treatments represent alternative embodiments of the present invention.

In some preferred embodiments of the invention, the recombinant bacterium that produces CRM 197 is a reduced genome bacterium. A "reduced genome" bacterium as used herein means a bacterium having about 1% to about 75% of its genome (e.g. protein coding genes) deleted, for example about 5%, about 10%, about 20%, about 30% about 40%, about 50% or about 60% of the genome deleted. In one embodiment, the reduced genome bacteria used in the practice of the present invention have a genome that is preferably genetically engineered to be at least two percent (2%) and up to thirty percent (30%) (including any number there between) smaller than the genome of a native parent strain. Preferably, the genome is at least two percent (2%) and up to twenty five percent (25%) smaller than the genome of a native parent strain. The genome may be about two percent (2%), five percent (5%), eight percent (8%), fourteen percent (14%), twenty percent (20%), twenty-five percent (25%), thirty percent (30%) (including any number there between) or more smaller than the genome of the native parent strain. Alternatively, the genome may be engineered to be less than 10%, less than 15%, less than 20% or less than 30% smaller than the genome of a native parental strain. The term "native parental strain" means a bacterial strain found in a natural or native environment as commonly understood by the scientific community to represent the foundation of a strain line and on whose genome a series of deletions can be made to generate a bacterial strain with a smaller genome. Native parent strain also refers to a strain against which the engineered strain is compared and wherein the engineered strain has less than the full complement of the native parent strain. The percentage by which a genome has become smaller after a series of deletions is calculated by dividing "the total number of base pairs deleted after all of the deletions" by "the total number of base pairs in the genome before all of the deletions" and then multiplying by 100 Similarly, the percentage by which the genome is smaller than the native parent strain is calculated by dividing the total number of nucleotides in the strain with the smaller genome (regardless of the process by which it was produced) by the total number of nucleotides in a native parent strain and then multiplying by 100.

In one embodiment, a "reduced genome" bacterium means a bacterium for which removal of the above amounts of genome does not unacceptably affect the ability of the organism to grow on minimal medium. Whether removal of two or more genes "unacceptably affects" the ability of the organism to grow on minimal medium in the present context depends on the specific application and is readily assessed. For example, a 30% reduction in proliferation rate may be acceptable for one application but not another. In addition, adverse effect of deleting a DNA sequence from the genome may be reduced by measures such as changing culture conditions. Such measures may turn an otherwise unacceptable adverse effect to an acceptable one. In one embodiment, the proliferation rate is approximately the same as the parental strain. However, proliferation rates ranging from about 5%, 10%, 15%, 20%, 30%, 40% to about 50% lower than that of the parental strain are within the scope of the invention. More particularly, doubling times of bacteria of the present invention may range from about fifteen minutes to about three hours. Non-limiting examples of suitable reduced genome bacteria, as well as methods for cumulatively deleting genomic DNA from a bacterium such as $E.$ $coli$, are disclosed in U.S. Pat. Nos. 6,989,265, 7,303,906, 8,119,365, 8,039,243, 8,178,339, and 9,902,965, each of which is hereby incorporated by reference herein.

The parental $E.$ $coli$ strain in the context of a reduced genome bacterium may be any $E.$ $coli$ strain. In some preferred embodiments, the parental $E.$ $coli$ strain is a K-12 strain (e.g. MG1655 (GenBank Accession No. U00096.3), W3110 (GenBank Accession No. AP009048.1), DH10B (GenBank Accession No. CP000948.1), DH1 (GenBank Accession No. CP001637.1), or BW2952 (GenBank Accession No. CP001396.1)). In other embodiments, the parental $E.$ $coli$ strain is a B strain (e.g. BLR(DE3) (GenBank Accession No. CP020368.1), REL606 (GenBank Accession No. CP000819.1), BL21(DE3) (GenBank Accession No. CP001509.3)).

In one aspect, the parental $E.$ $coli$ strain is a K-12 or B strain lacking one or more of the genes listed at Tables 2-20 of U.S. Pat. No. 8,178,339, incorporated herein by reference. In a preferred embodiment, the reduced genome $E.$ $coli$ K-12 or B strain lacks at least the following genes of the $E.$ $coli$ K-12 strain MG1655 (identified by "b" numbers based on the designations set out in Blattner et al., Science, 277:1453-74 and in GenBank Accession No. U00096.3): b0245-b0301, b0303-b0310, b1336-b1411, b4426-b4427, b2441-b2450, b2622-b2654, b2657-b2660, b4462, b1994-b2008, b4435, b3322-b3338, b2349-b2363, b1539-b1579, b4269-b4320, b2968-b2972, b2975-b2977, b2979-b2987, b4466-b4468, b1137-b1172, b0537-b0565, b0016-b0022, b4412-b4413, b0577-b0582, b4415, b2389-b2390, b2392-b2395, b0358-b0368, b0370-b0380, b2856-b2863, b3042-b3048, b0656, b1325-b1333, b2030-b2062, b2190-b2192, b3215-b3219, b3504-b3505, b1070-b1083, b1878-b1894, b1917-b1950, b4324-b4342, b4345-b4358, b4486, b0497-b0502, b0700-b0706, b1456-b1462, b3481-b3484, b3592-b3596, b0981-b0988, b1021-b1029, b2080-b2096, b4438, b3440-b3445, b4451, b3556-b3558, b4455, b1786, b0150-b0153 and b2945, which are the genes deleted from MG1655 to create MDS42, or lacks the corresponding genes in another $E.$ $coli$ K12 or B strain. In still another embodiment, the reduced genome $E.$ $coli$ K-12 or B strain further lacks at least the following genes: b0315-b0331, b0333-b0341 and b0346-b0354, b2481-b2492, b2219-b2230, b4500, b3707-b3723, b0644-b0650, b4079-4090, b4487, b4092-b4106, b0730-b0732, b3572-b3587, b1653, b2735-b2740, b2405-b2407, b3896-b3900, b1202, b4263-b4268, b0611, b2364-b2366, b0839, b0488-b0500, b0502, b0566-b0575, b2209, b0160-b0161, b1431-b1444, b3643, b1037-b1043, b0383, b0226-b0234, and b2115-b2132, which are the genes deleted from MDS42 to create MDS69. In certain embodiments, the reduced genome $E.$ $coli$ K-12 strain for use in the methods described herein is MDS42 or MDS69.

Recombinant bacteria that produce CRM 197 may comprise a functional recA gene (b2699) or may lack a functional recA gene (b2699). For example, a reduced genome $E.$

*coli* strain such as e.g. strain MDS42 or MDS69 can be modified by inactivation of b2699 by complete or partial deletion of the gene from the modified *E. coli* K-12 strain.

In one embodiment, CRM 197 is produced according to the methods described in United States Patent Application Publication No. 20170073379, the entire disclosure of which is incorporated herein by reference. In particular, paragraphs [0055]-[0059] describe a method of producing CRM 197 in the periplasm by growing *E. coli* bacterium comprising an expression vector comprising a nucleotide sequence encoding a CRM 197 protein fused to a signal sequence that directs transfer of the CRM 197 protein to the periplasm, said nucleotide sequence operably linked to an expression control sequence, under conditions suitable for expression of CRM 197. Representative signal sequences capable of directing CRM 197 to the periplasm are listed at the end of paragraph [0057] of US 20170073379 and preferably are selected from an OmpA, MalE, HdeA, OppA, HdeB, GlnH, Mg1B, agp, OmpC, RbsB, FkpA or YtfQ signal sequence, more preferably from an OmpA, OmpF or YtfQ signal sequence.

In an embodiment of the present invention insoluble material within the bacterial cell lysate is removed prior to chromatographic purification. In one embodiment the bacterial cell lysate is treated with a chaotropic salting agent and a flocculent. In some embodiments the chaotropic agent may be ammonium sulfate, lithium acetate, or guanidium chloride. In some embodiments the floculant may be an inorganic floculent including ferric chloride, ferric sulfate, polyaluminum chloride or sodium aluminate. In other embodiments the floculent may be a natural floculent such as chitosan, gelatin, alginate, or guar gum. In still other embodiments synthetic organic floculents such as polyacrylamide or polydiallyldimethylammonium chloride (pDAD-MAC). In a preferred embodiment the bacterial cell lysate is treated by adding an equal volume of a solution comprising 50 mM Tris, 2 M ammonium sulfate, and 2 M sodium acetate pH 8.0 slowly with constant stirring over a 5 minute period and polydiallyldimethylammonium chloride added to a final concentration of 0.1%. In an embodiment an additional clarifying agent, such as activated charcoal or carbon black is added to the bacterial cell lysate. In a preferred embodiment Norit CA1 is added to final concentration of about 1.0%. In an embodiment the solids within the bacterial cell lysate treated with chaotropic salts, floculents, clarifying agents, or any combinations thereof are removed by allowing them to settle under gravity, centrifugation, or filtration. In a preferred embodiment the treated bacterial cell lysate is mixed vigorously for about 30 minutes at room temperature and then centrifuged for 30 minutes at 16,000 g and the resulting clarified supernatant decanted from the precipitate.

In an embodiment the clarified supernatant is treated with a protease inhibitor such as 4-(2-aminoethyl) benzene sulfonyl fluoride hydrochloride (AEBSF), E-64, leupeptin, or 1,10-phenanthroline. In a preferred embodiment AEBSF is added to a final concentration of about 0.3 mM. In an embodiment the clarified supernatant is then filtered to remove any remaining insoluble materials. In a preferred embodiment the clarified supernatant is filtered in two stages. The first stage utilizes depth filters with an exclusionary range of about 3 to 0.8 microns. The stage involves filtering the first stage filtrate across 0.45-0.2 micron filters.

In an embodiment the clarified supernatant or filtrate containing CRM 197 is further purified by binding the CRM 197 to one or more separation agents, such as one or more chromatographic resins. The chromatographic resin may be a hydrophobic interaction resin, an anion exchange resin, a cation exchange resin, a mixed mode resin or a hydroxyapatite resin. In one embodiment the CRM 197 is bound to the chromatographic resin in a batch capture mode, wherein the resin and the sample are mixed together, the CRM 197 is allowed to bind the resin, the liquid phase is removed by filtration or by allowing the bound resin to settle, and the remaining liquid decanted. In another embodiment the chromatography resin is held stationary within a column and the solution containing CRM 197 is allowed to pass over or the resin within the column under conditions suitable for the CRM 197 to bind to the chromatographic resin. In some embodiments the chromatography resin bound with CRM 197 is washed with a buffer that does not elute the CRM 197 from the resin but may remove contaminating material prior to exposing the resin to a different buffer capable of eluting CRM 197 from the chromatography resin.

In one embodiment, purification of CRM 197 comprises (i) a hydrophobic interaction chromatography step, (ii) an anion exchange chromatography step in flow-through mode, (iii) an anion exchange chromatography step in bind/elute mode and (iv) a hydroxyapaptite chromatography step, preferably in that order.

In preferred embodiments, purification of CRM 197 comprises a mixed mode cation exchange/hydrophobic interaction chromatography step, optionally followed by one or more additional purification steps. In a particularly preferred embodiment, purification of CRM 197 comprises (i) a mixed mode cation exchange/hydrophobic interaction chromatography step followed by (ii) an anion exchange chromatrophy step in bind/elute mode and (iii) a hydroxyapatite chromatography step, wherein steps (ii) and (iii) are performed in either order. According to these embodiments, high yield purification of CRM 197 is accomplished with a reduced number of chromatography steps and without the need for diafiltration, e.g. prior to anion exchange chromatography. In a particularly preferred embodiment, purification of CRM 197 comprises (i) a mixed mode cation exchange/hydrophobic interaction chromatography step followed by (ii) a hydroxyapatite chromatography step followed by (iii) an anion exchange chromatography in bind/elute mode, wherein the eluates from step (i) and step (ii) do not require dilution or diafiltration prior to steps (ii) and (iii) respectively.

In some embodiments, purification of CRM 197 comprises hydrophobic interaction chromatography, wherein the clarified filtrate or supernatant comprising CRM 197 or an eluate comprising CRM 197 from a previous chromatographic purification step is loaded onto a hydrophobic interaction column equilibrated with a high salt aqueous buffer. The salt may be ammonium sulfate or sodium chloride at a concentration between 1 M and 3 M, preferably, between 1 M and 2 M, more preferably about 1 M and the aqueous buffer may have a pH of between 7.0 and 9.0, preferably at about 8.0. In some embodiments the column is washed with a high salt buffer and the CRM 197 subsequently eluted with a salt-free or low salt buffer. CRM 197 can also be eluted by gradient elution (as the salt concentration is lowered, CRM 197 becomes increasingly desorbed). In a preferred embodiment the wash buffer comprises 25 mM Tris, 1 M ammonium sulfate, 1 M sodium acetate pH 8.0 and the CRM 197 is eluted from the column in 25 mM Tris pH 8.0. In other embodiments, the wash buffer comprises 1 M to 3 M of a different salt such as sodium chloride. The hydrophobic chromatography resin preferably comprises a chemical with a weak hydrophobicity (e.g. ether) or an intermediate hydrophobicity (e.g. PPG-600M, Phenyl-650S, Phenyl-650C, Phenyl-600M). In preferred embodiments, the hydrophobic chromatography resin comprises polypropylene glycol (e.g. PPG-600M) bonded to polymethylacrylate. In some embodiments, the initial (first) chromatographic purification step comprises hydrophobic interaction chromatography column.

In an embodiment additional redox agent and protease inhibitor may be added to the CRM 197 containing solutions after one or more purification steps. In a preferred embodiment AEBF and glutathione disulfide, respectively, are added to the CRM 197 recovered from the hydrophobic interaction chromatography step to about 1 mM final concentration each. In some embodiments the volume of the pooled fractions obtained with one or more chromatography purification steps may be reduced by ultrafiltration and the solution equilibrated by diafiltration to ensure that the sample is compatible with the second separation agent. Preferably, the volume of the pooled fractions obtained from the hydrophobic interaction chromatography step is reduced by ultrafiltration and the solution equilibrated by diafiltration to ensure that the sample is compatible with anion exchange chromatography.

In preferred embodiments, purification of CRM 197 comprises mixed mode cation exchange chromatography (preferably cation exchange/hydrophobic interaction chromatography), wherein the clarified filtrate or supernatant comprising CRM 197 or an eluate comprising CRM 197 from a previous chromatographic purification step is loaded onto a mixed mode cation exchange column comprising ligands which comprise a hydrophobic part and a negatively charged part. In some embodiments, CRM 197 is loaded onto the column at a pH of between 6.5 and 7.0, preferably about 6.75, and a conductivity below about 11 mS/cm, preferably a conductivity of about 10 mS/cm. In some embodiments the column is washed with 50-500 mM NaCl at a pH between 6.5 and 7.0, preferably about 6.75 and/or 10-50 mM arginine at a pH between 6.5 and 7.0, preferably about 6.75. CRM 197 can be eluted at high pH and/or conductivity. In a preferred embodiment the wash buffer comprises 100 mM NaCl, pH 7.0 and/or 20 mM arginine pH 7.0 and CRM 197 is eluted from the column in a buffer comprising about 750 mM to 1.3 M arginine, preferably about 1 M arginine at a pH of between 8.0 and 9.5, preferably at a pH of about 9. In some preferred embodiments, an initial (first) chromatographic purification step of CRM 197 following its production in a bacterial host comprises mixed mode cation exchange chromatography.

In preferred embodiments, purification of CRM 197 comprises anion exchange chromatography, wherein the clarified filtrate or supernatant comprising CRM 197 or an eluate comprising CRM 197 from a previous chromatographic purification step is further purified by passing the CRM 197 over an anion exchange column under conditions such that CRM 197 does not bind to the resin (i.e. flow-through mode), but contaminant proteins (i.e. negatively charged impurities) do bind. In a preferred embodiment the anion exchange resin is a strong anion exchange resin e.g. one that comprises a quaternary amine attached to polymethacrylate beads. In a preferred embodiment the CRM 197 is passed through the column in a buffer comprising about 50 mM NaCl to about 300 mM NaCl at a pH between about 7.0 to 9.0, more preferably in a buffer comprising about 150 mM NaCl at a pH of about 8.0. In some embodiments, an initial (first) chromatographic purification step of CRM 197 comprises hydrophobic interaction chromatography column and a second purification step comprises anion exchange resin operated in flow-through mode.

In other preferred embodiments, purification of CRM 197 comprises anion exchange chromatography, wherein the clarified filtrate or supernatant comprising CRM 197 or an eluate comprising CRM 197 from a previous chromatographic purification step is further purified by passing the CRM 197 over an anion exchange column under conditions such that CRM197 binds to the resin but contaminant proteins do not bind (i.e. bind/elute mode). In preferred embodiments, the anion exchange resin operating in bind/elute mode is a strong anion exchange resin e.g. one that comprises a quaternary amine attached to polymethacrylate beads. In a preferred embodiment, (i) the anion exchange column is equilibrated with a buffer comprising about 50 mM NaCl (ii) the CRM 197 is loaded onto the anion exchange column in a buffer comprising 50 mM NaCl and (iii) the CRM 197 is eluted in a buffer comprising at least 200 mM NaCl, preferably at a pH of about 8.0. In some embodiments the CRM 197 is eluted from the anion exchange column using a step gradient. In a preferred embodiment the CRM 197 is eluted from the anion exchange column using a linear elution gradient. In a particularly preferred embodiment, a segment of the linear elution gradient comprises at least 200 nM NaCl, more preferably between 200-280 mM NaCl. In related embodiments, the anion exchange resin operated in bind/elute mode is identical to the anion exchange resin operated in flow-through mode in a different (e.g. previous) CRM 197 purification step. In preferred embodiments, an initial (first) chromatographic purification step comprises hydrophobic interaction chromatography, a second chromatographic purification step comprises anion exchange chromatography in flow-through mode and a third chromatographic purification step comprises anion exchange chromatography operated in bind/elute mode.

In other preferred embodiments, purification of CRM 197 comprises hydroxyapatite chromatography, wherein the clarified filtrate or supernatant comprising CRM 197 or an eluate comprising CRM 197 from a previous chromatographic purification step is further purified by loading CRM 197 onto a hydroxyapatite column. In some embodiments, (i) the hydroxyapatite column is equilibrated in a buffer comprising 2 mM $NaPO_4$ (ii) CRM 197 is loaded onto the hydroxyapatite column in a buffer comprising about 2 mM $NaPO_4$ and (iii) CRM 197 is eluted in a buffer comprising 150 mM $NaPO_4$. In other embodiments, (i) the hydroxyapatite is equilibrated in buffer (preferably about 25 mM HEPES), 2 mM $CaCl2$, pH about 8.0 (ii) CRM 197 is loaded onto the hydroxyapatite column in 25 mM HEPES, +/−2 mM $CaCl2$, pH 8.0 and (iii) CRM 197 is eluted with a linear gradient to 25 mM HEPES, 2 mM $CaCl2$, 1 M sodium sulfate, pH about 8.0. In some embodiments the CRM 197 is eluted from the hydroxyapatite column using a step gradient. In a preferred embodiment the CRM 197 is eluted from the hydroxyapatite column using a linear elution gradient. In some preferred embodiments, CRM 197 is eluted using a linear (or step) elution gradient from 2 mM to 150 mM $NaPO_4$. In other preferred embodiments, CRM 197 is eluted using a linear (or step) elution gradient up to 1 M sodium sulfate.

CRM 197 has a propensity to dimerize in solution. See e.g. Malito et al., PNAS 109(14):5229-5234 (2012). Importantly, CRM 197 must be in monomer form so that lysine amines are accessible for conjugation. In some embodiments, a solution comprising CRM 197 is subjected to heat treatment to dissociate CRM 197 dimers to monomer form following one or more purification steps. In preferred embodiments, heat treatment comprises incubation at 37° C.

for at least 30 minutes, at least 40 minutes, at least 50 minutes at least 60 minutes, at least 2 hours, at least 3 hours. Preferably, heat treatment comprises incubation at 37° C. for between 30 minutes and 90 minutes, more preferably for about 60 minutes. The presence of CRM 197 dimers following one or more purification steps can be detected and quantified using e.g. size exclusion high performance liquid chromatography. In some embodiments, a solution comprising CRM 197 is tested for the presence of CRM 197 dimers following one or more purification steps.

In some embodiments the purified CRM 197 may be combined with pharmaceutically acceptable excipients. In some embodiments CRM 197 is stored as an aqueous solution. In still other embodiments CRM 197 may be freeze dried and stored as a dry powder.

EXAMPLES

The following examples are meant to be illustrative of the invention and is not intended to limit the scope of the invention as set out in the appended claims.

Example 1

Figure 2:
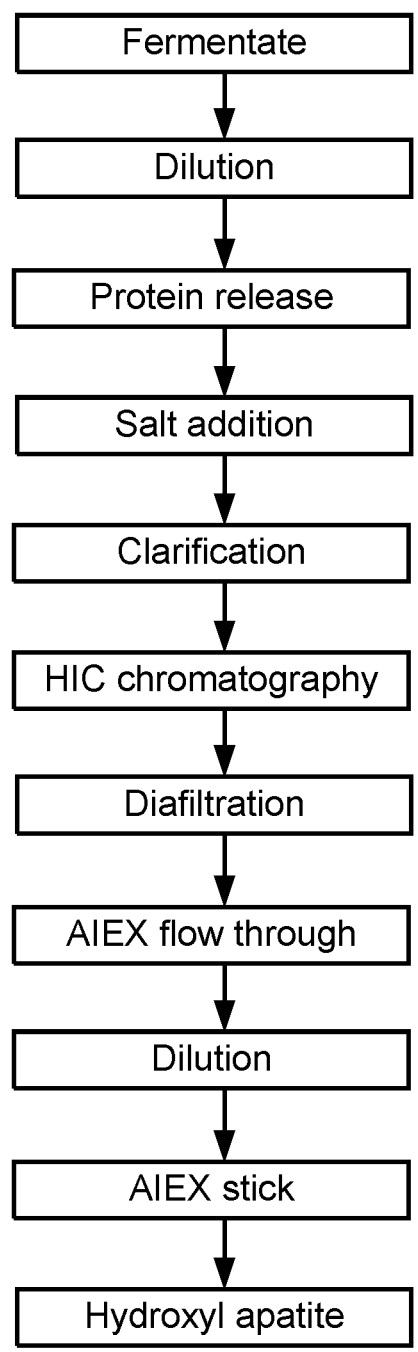
FIG. 2 illustrates an embodiment of a purification scheme for CRM 197. Briefly, fermentate from an *E. coli* host expressing CRM 197 is diluted with an equal volume of solubilizing agent (L-arginine, pH 8.0 is exemplified) and a redox agent is added (1 mM glutathione disulfide is exemplified) to the diluted fermentate. The bacterial cells within the oxidized mixture are then lysed (microfluidizer is exemplified) to release CRM 197. A chaotropic salting agent (ammonimum sulfate is exemplified), a flocculent (pDAD-MAC [poly (diallyldimethyl-ammonium chloride)] is exemplified) and activated charcoal or carbon black (Norit CA1 is exemplified) were added to the lysate. The lysate was then clarified (i.e. insoluble material was removed) by centrifugation and filtration and the clarified supernatant was then subjected to (i) hydrophobic interaction chromatography (HIC) and (ii) the diafiltered HIC eluate was subjected to anion exchange chromatography (AIEX) in flow-through mode and (iii) the diluted AIEX flow-through fractions was subjected to AIEX in bind/elute mode and (iv) the AIEX eluate was subjected to hydroxyapatite chromatography.
Figure 3:
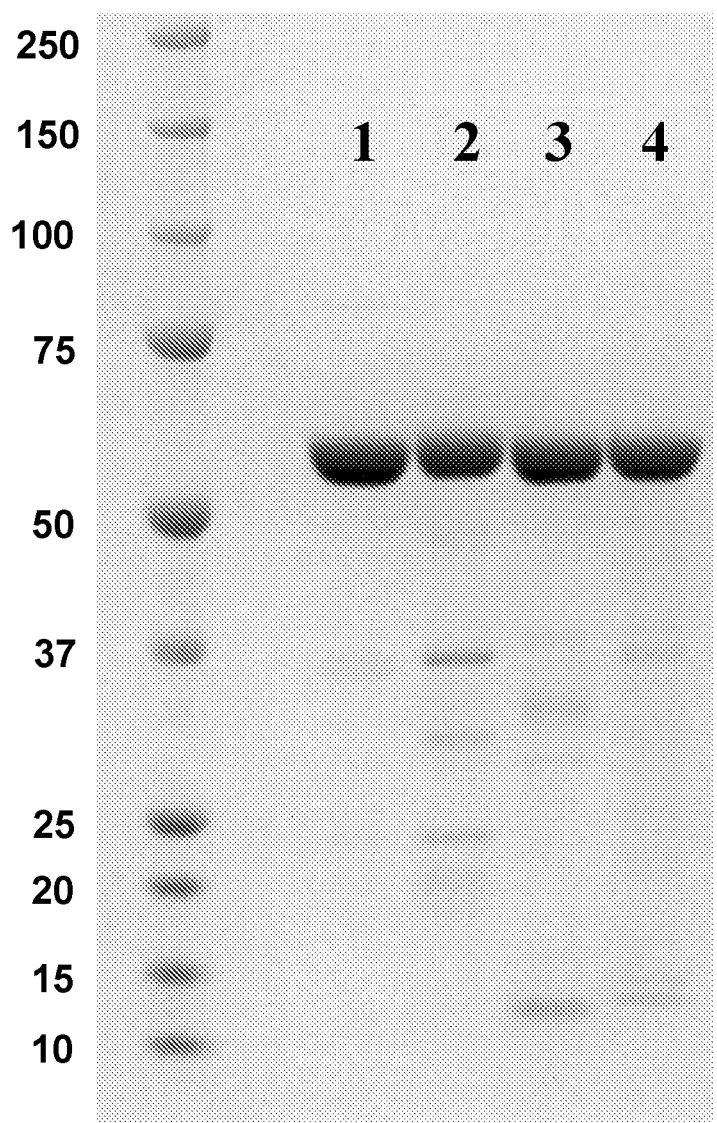
FIG. 3 illustrates the purity of CRM 197 prepared by the purification scheme depicted in FIG. 2 relative to commercial CRM 197 preparations by denaturing and reducing PAGE analysis. PAGE, marker, and sample conditions are as described in FIG. 1, with DTT treatment. Sample lane 1 is CRM 197 produced by the present invention, sample lane 2 is CRM 197 from List Biological Laboratories, sample lane 3 is CRM 197 from MBL International, and sample lane 4 is CRM 197 from Fina Biosolutions.

Recovery of CRM 197 from a Bacterial Fermentate Using the Purification Scheme of FIG. 2
Cell Lysis.

Bacterial fermentate containing cells and media were processed by thawing (if frozen) and addition of an equal volume of 750 mM L-arginine pH 8.0. The mixture was thoroughly blended and glutathione disulfide (oxidized L-glutathione) added to a final concentration of about 1 mM. The oxidized mixture was then passed through a microfluidizer (Microfluidics M-110P, Microfluidics Corp., Westwood, Mass.) at least two passes at 14,000 to 16,000 psi to ensure complete cell lysis. The lysate was kept on ice until further processing. The following experiments were performed with CRM 197 samples ranging from 0.7 g/l to 4.6 g/l CRM 197. Starting with an estimated total of about 3 g of CRM 197, recovery of at least about 1.0-1.5 grams CRM 197 in the final formulation is obtainable. All chromatographic purification steps were carried out at room temperature unless otherwise indicated. For each chromatographic purification step, several salt concentrations and pH ranges were tested to maximize CRM 197 recover and contaminant removal.
Clarification To clarify the lysate an equal volume of a solution comprising 50 mM Tris, 2 M ammonium sulfate, and 2 M sodium acetate pH 8.0 was slowly added with constant stirring over a 5 minute period. pDADMAC was added to a final concentration of 0.1%. The clarifying agent, Norit CA1 was then added to final concentration of about 1.0%. Other carbons such as Norit CA3, Darco G60, Norit CA1 were tried but did not work as well as Norit CAL The solution was mixed vigorously for about 30 minutes at room temperature and then centrifuged for 30 minutes at 16,000 g and the supernatant decanted from the precipitate. The supernatant was treated with the protease inhibitor such as 4-(2-aminoethyl) benzene sulfonyl fluoride hydrochloride (AEBSF) at a final concentration of about 0.3 mM. The treated supernatant may be passed through Miracloth to remove large particulates. The supernatant was then filtered in two stages. The first crude filtration stage involved removal of remaining particulates by filtration across depth filters with an exclusionary range of about 3 to 0.8 microns. The second fine filtration stage involved filtering the first stage filtrate across 0.45-0.2 micron filters. The resulting fine filtrate was kept on ice until further processing.
Hydrophobic Interaction Chromatography The filtrate was loaded onto a hydrophobic interaction column (Tosoh PPG 600M column, 5 cm×40 cm, 770 ml c.v.) equilibrated with 25 mM Tris, 1 M ammonium sulfate, 1 M sodium acetate pH 8.0. The column was washed with 5 c.v. of 25 mM Tris, 1 M ammonium sulfate, 1 M sodium acetate pH 8 buffer and the CRM 197 eluted (approx. 80%) in 4 c.v. of 25 mM Tris pH 8.0 (with a conductivity of about 1.3 mS/cm). Typically, each c.v. was collected as a separate fraction. The fractions containing the bulk of the CRM 197 were pooled and kept on ice until further processing.
Filtration and Diafiltration AEBSF and oxidized glutathione were added to the pooled CRM 197 containing fractions to a final concentration of about 1 mM each. The volume of the pooled fractions was reduced to about half of the initial volume by ultrafiltration across a Spectrum M12S-600-01N polysulfone filter ($2\times8,000$ cm$^2$ 10 K UF) via tangential flow filtration and diafiltered against about 5 initial volumes of 25 mM Tris, 150 mM NaCl pH 8.0. The diafiltered samples were held on ice until further processing.
Anion Exchange Chromatography (Flow Through)

The equilibrated pooled CRM 197 sample were passed over an anion exchange column (Tosoh GigaCap Q 650M, 4.8 cm×47 cm, 850 ml c.v.) equilibrated with 25 mM Tris, 150 mM NaCl, pH 8.0. Fractions were collected once the OD$_{280}$ of the outflow rose above 0.1, the column was continuously washed with 25 mM Tris, 150 mM NaCl, pH 8.0 and fractions collected until the OD$_{280}$ of the outflow fell below 0.1 (about 3 additional c.v.). The protein containing fractions were pooled and held on ice until further processing.
Anion Exchange Chromatography (Bind and Elute)

Several dilutions of the pooled flow-through fractions were tested to optimize retention of CRM 197 and minimize volume. Best results were obtained by diluting the pooled flow-through fractions 1:3 (two parts buffer with 1 part pooled fractions) with 25 mM Tris, pH 8.0. An anion exchange column (Tosoh GigaCap Q 650M, 2.6 cm×38.5 cm, 204 ml c.v.) was equilibrated with 25 mM Tris, 50 mM NaCl, pH 8.0 and the diluted pooled fractions applied to the column. A linear gradient from 50 mM to 280 mM NaCl (in Tris, pH 8.0 buffer) was used to recover protein from the column, with CRM 197 eluting between 200-280 mM NaCl. The CRM 197 containing fractions were pooled and held on ice until further processing.
Hydroxyapatite Chromatography The pooled CRM 197 containing fractions were modified by adding ½$_{50}$th volume of a buffer comprising 25 mM HEPES, 150 mM NaCl, 500 mM NaPO$_4$ at pH 7.4. A Tosoh CaPure Hydroxyapetite (HA) column (5 cm×21 cm, 412 ml c.v.) was equilibrated with 25 mM HEPES, 150 mM NaCl, 2 mM NaPO$_4$, pH 7.4. The modified pooled CRM 197 was loaded onto the column at 60 cm/hr and the column was then washed with about 5 c.v. of 25 mM HEPES, 150 mM NaCl, 2 mM NaPO$_4$, pH 7.4 at 120 cm/hr. The CRM 197 was eluted from the HA column with a 3 c.v. linear gradient from 2 mM to 150 mM NaPO$_4$ (in 25 mM HEPES, 150 mM NaCl, pH 7.4) at 120 cm/hr, followed by an additional c.v. of 25 mM HEPES, 150 mM NaCl, 150 mM NaPO4, pH 7.4 also at 120 cm/hr. The HA eluate fractions were pooled and held on ice until further processing. In parallel experiments, the hydroxyapatite was equilibrated in 25 mM HEPES, 2 mM CaCL2, pH 8.0 and CRM 197 was loaded onto the hydroxyapatite column in 25 mM HEPES, 2 mM CaCl2, pH 8.0, (or the same buffer without CaCl2-CaCl2 is not necessary in the loading buffer but improves column stability which may lead to increased CRM 197 binding) followed by elution of CRM 197 with a linear gradient to 25 mM HEPES, 2 mM CaCl2, 1 M sodium sulfate, pH 8.0, with slightly improved yield and purity of CRM 197.

Concentration

The protein concentration of the pooled HA eluate fractions was determined and adjusted to a pool concentration of 3.8-4.2 mg/ml by tangential flow filtration as described above.

Fill Finish

To produce a dry purified CRM 197 product, the filtrate/retentate was diafiltered against about 5 volumes of storage buffer (10 mM NaPO4, 5% lactose), the desired amount of purified CRM 197 was aliquoted into storage vials and lyophilized. The lyophilized CRM 197 is stored at −20° C. or −80° C. To produce a liquid purified CRM 197 product, the filtrateketentate was diafiltered about least 5 volumes of storage buffer (25 mM HEPES, 150 mM NaCl, pH 7.4), the desired amount of CRM 197 was aliquoted into storage buffers and flash frozen. The frozen CRM 197 is stored at −80° C.

Example 2

Figure 4:
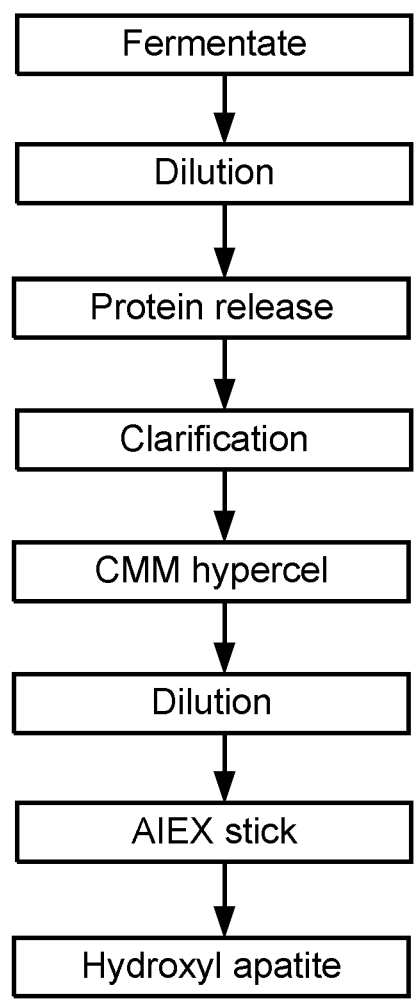
FIG. 4 illustrates a further optimized embodiment of a purification scheme for CRM 197. Briefly, an *E. coli* host expressing CRM 197 in which CRM 197 is transported to the media was used to produce CRM 197. Media containing CRM 197 was collected and centrifuged and the resulting supernatant diluted 1:3 with 25 mM MOPS pH 7.0 and (i) directly loaded onto a mixed mode cation exchange/hydrophobic interaction chromatography (CMM hypercel) and the diluted eluate from (i) was subjected to (ii) AIEX chromatrophy in bind/elute mode and the eluate from (ii) was subjected to (iii) hydroxyapatite chromatography. This embodiment eliminates the need for addition of a flocculating agent, a chaotropic salt and activated carbon to the original fermentate prior to clarification and does not require a hydrophobic interaction chromatography (HIC) step, diafiltration of the HIC eluate and an AIEX flow-through chromatography step. Reduction of conductivity, via dilution or diafiltration, is required for binding onto an AIEX bind/elute chromatography step, but the eluate from the AIEX can be used directly for binding on the hydroxylapatite resin.
Figure 5:
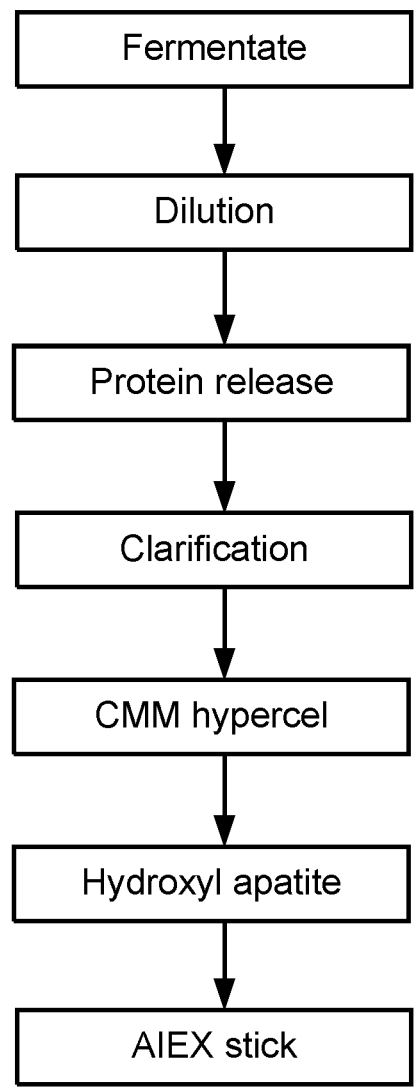
FIG. 5 illustrates a yet further optimized embodiment of a purification scheme for CRM 197, which is identical to the purification scheme depicted in FIG. 4, except that the eluate from mixed mode cation exchange/hydrophobic interaction chromatography is directly loaded onto a hydroxyapatite column (without dilution or change in conductivity) and the eluate from hydroxyapatite chromatography is loaded onto the AIEX column (in bind/elute mode). Reversal of the hydroxyapatite chromatrophy and AIEX chromatography steps eliminates the need to dilute the pooled fractions from mixed mode cation exchange/hydrophobic interaction chromatography.

Recovery of CRM 197 Using the Purification Scheme of FIG. 4

Clarification

In this experiment, a strain of reduced genome bacteria that secretes CRM 197 into the media was used to produce CRM 197; however, the following purification procedure can also be used to purify CRM 197 produced in the cytosol or periplasm of any suitable *E. coli* host strain. The media containing CRM 197 was centrifuged for 30 minutes at 16,000 g and the supernatant decanted from the precipitate. The supernatant was then filtered across a 0.22 micron filter and then diluted 1 part supernatant:3 parts 25 mM MOPS pH 7.0 to reduce the conductivity below 11 mS/cm.

Mixed Mode Cation Exchange/Hydrophobic Interaction Chromatography

The diluted filtrate was directly loaded onto a mixed mode cation exchange/hydrophobic interaction chromatography column (Pall Life Sciences CMM HyperCel) equilibrated with 25 mM MOPS pH 7.0. Several binding conditions were tested (pH 6.0-7.5 and various conductivities) with pH 6.5-7.0, particularly 6.75, and conductivity below about 11 mS/cm achieving optimal results. CMM HyperCel resin comprises a ligand containing both a carboxyl group and a benzene ring, conferring cation exchange and hydrophobicity properties respectively. At a pH of 4-9, the amine group is not charged. The carboxyl group is weakly charged at adsorption pH (4 to 6) to allow protein adsorption based on hydrophobicity. At elution pH (7 to 9), the carboxyl group is fully deprotonated and elution is based on negative charge repulsion. Several combinations of different wash and elution buffers were tested. Washing with 100 mM NaCl was found to remove many contaminants with minimal loss of CRM 197. Optimal results were achieved by washing the column with 25 mM MOPS, 100 mM NaCl pH 7.0. Arginine was found to be the best eluent from among several tested eluents (e.g. NaCl or MgCl2, each of which resulted in a less than 80% recovery of CRM 197), with superior results achieved at high pH (8.0-9.5) and high arginine concentration (0.5 to 1.5 M arginine). Optimal results were achieved by eluting CRM 197 in 1 M arginine, pH 9.0. Typically, each c.v. was collected as a separate fraction. Recovery of CRM 197 was determined to be greater than 80%, with greater than 80% purity obtained. Employing an initial mixed-mode chromatographic purification step in the purification of CRM 197 resulted in high yield and purity, and replaced two chromatographic purification steps (HIC and AIEX in flow-through mode) of the purification procedure of Example 1. The fractions containing the bulk of the CRM 197 were pooled and kept on ice until further processing. The optimal binding and elution conditions were determined empirically. Surprisingly, CRM 197 bound to the column at pH of 6.5-7.0, above its isoelectric point and was eluted with 1 M arginine at pH 9.0. Based on the results of this experiment, recovery of 80% to 95% of CRM is obtainable.

Filtration and Diafiltration

The CMM eluate was diluted 1:1 with 25 mM tris pH 8.0 to reduce conductivity. Alternatively, the volume of the pooled CMM fractions may be reduced to about half of the initial volume by ultrafiltration across a Spectrum M12S-600-01N polysulfone filter (2×8,000 $cm^2$ 10 K UF) via tangential flow filtration and diafiltered against about 5 initial volumes of 25 mM Tris, 50 mM NaCl pH 8.0. AEBSF and oxidized glutathione may be added to the pooled CRM 197 containing fractions to a final concentration of about 1 mM each.

Anion Exchange Chromatography (Bind and Elute)

The pooled fractions were directly applied to an anion exchange column (Tosoh GigaCap Q 650M, 2.6 cm×38.5 cm, 5 ml c.v.) equilibrated with 25 mM Tris, 50 mM NaCl, pH 8.0. A linear gradient from 50 mM to 280 mM NaCl (in Tris, pH 8.0 buffer) was used to recover protein from the column, with CRM 197 eluting between 200-280 mM NaCl. The CRM 197 containing fractions were pooled and held on ice until further processing.

Hydroxyapetite Chromatography

The pooled CRM 197-containing fractions were modified by adding $\frac{1}{250}^{th}$ volume of a buffer comprising 25 mM HEPES, 500 mM CaCl2, pH 8.0. A Tosoh CaPure Hydroxyapetite (HA) column (5 cm×21 cm, 412 ml c.v.) was equilibrated with 25 mM HEPES, 2 mM CaCl2, pH 8.0. The modified pooled CRM 197 was loaded onto the column at 60 cm/hr and the column was then washed with about 5 c.v. of, 25 mM HEPES, 2 mM CaCl2, pH 8.0 at 120 cm/hr. CRM 197 was eluted from the HA column with a 10 c.v. gradient to 25 mM HEPES, 2 mM CaCl2, 1 M sodium sulfate, pH 8.0. The HA eluate fractions were pooled and held on ice until further processing.

Example 3

Recovery of CRM 197 Using the Purification Scheme of FIG. 5

Clarification

In this experiment, a strain of reduced genome *E. coli* that secretes CRM 197 into the media was used to produce CRM 197; however, the following purification procedure can also be used to purify CRM 197 produced in the cytosol or periplasm of any suitable *E. coli* host strain. The media containing CRM 197 was centrifuged for 30 minutes at 16,000 g and the supernatant decanted from the precipitate. The supernatant was then filtered across a 0.22 micron filter and then diluted 1 part supernatant:3 parts 25 mM MOPS pH 7.0.

Mixed Mode Cation Exchange/Hydrophobic Interaction Chromatography

Mixed mode cation exchange/hydrophobic interaction chromatography was performed using the optimized conditions described in Example 2. Briefly, 10 ml of filtrate (A260=14.509; A280=8.440) was loaded directly onto a mixed mode cation exchange/hydrophobic interaction chromatography column (Pall Life Sciences CMM hypercel; 1 ml column 0.5×5 cm) equilibrated with 25 mM MOPS pH 6.75. The column was washed with 25 mM MOPS, 100 mM NaCl pH 7.0 and CRM 197 was eluted in 1 M arginine, pH 9.0. Typically, each c.v. was collected as a separate fraction. Recovery of CRM 197 was determined to be greater than 80%, with greater than 80% purity obtained. The fractions containing the bulk of the CRM 197 were pooled and kept on ice until further processing.

Hydroxyapetite Chromatography

The pooled CRM 197-containing fractions were modified by adding $\frac{1}{250}^{th}$ volume of a buffer comprising 25 mM HEPES, 500 mM CaCl2, pH 8.0. A Biorad CHT type I 40 uM column (1 ml column 0 8×2 cm) was equilibrated with 25 mM HEPES, 2 mM CaCl2, pH 8.0. The modified pooled CRM 197 was loaded onto the column at 60 cm/hr and the column was then washed with about 5 c.v. of, 25 mM HEPES, 2 mM CaCl2, pH 8.0 at 60 cm/hr. CRM 197 was eluted from the HA column with a 10 c.v. linear gradient to 25 mM HEPES, 2 mM CaCl2, 1 M sodium sulfate, pH 8.0. Alternatively, a step gradient may also be used to elute CRM 197 form the HA column. The HA eluate fractions were pooled and held on ice until further processing. Similar results were achieved using the Biorad type 1 column and the Tosoh CaPure columns. The purity and yield of CRM 197 following mixed-mode ion exchange chromatography and HA chromatography is suitable for commercial use; however, one or more additional purification steps may be employed such as anion exchange chromatography in bind/elute mode.

Anion Exchange Chromatography (Bind and Elute)

The conductivity of the pooled HA fractions may be reduced below 7.5 mS/cm by dilution and/or diafiltration and directly applied to an anion exchange column (Tosoh GigaCap Q 650M, 2.6 cm×38.5 cm, 204 ml c.v.) equilibrated with 25 mM Tris, 50 mM NaCl, pH 8.0. A linear gradient from 50 mM to 280 mM NaCl (in Tris, pH 8.0 buffer) is used to recover protein from the column, with CRM 197 eluting between 200-280 mM NaCl. The CRM 197 containing fractions are pooled and held on ice until further processing.

Example 4

Heat Treatment of an Excipient-Free Liquid Formulation Comprising CRM 197 Following Long Term Storage at −80 C.

The stabilization of purified CRM 197 in a formulation comprising HEPES buffer without excipients (such as a saccharide or polyol) was assessed. The presence of dimers in the purified CRM 197 solution was detected and quantified using size exclusion high performance liquid chromatography (sec-HPLC).

Purified CRM 197 was stored in 25 mM HEPES, 150 mM NaCl, pH 7.4 at −80° C. (formulation B). Samples (1104B) were thawed at room temperature and analyzed by sec-HPLC (control) or heated to 37° C. for various times prior to analysis.

Sec-HPLC analysis was performed on a Dionex Ultimate 3000 instrument equipped with an autosampler, diode array detector and a Phenomenex Yarra 1.7 μm column (4.6×300 mm). The column was equilibrated and run using a buffer consisting of 50 mM sodium phosphate, 100 mM NaCl, 0.02% sodium azide, pH 7.5. Samples were diluted with running buffer to 0.5 mg/ml and filtered through a 0.22 μm filter prior to loading. Twenty microliters of diluted and filtered sample were loaded onto the column. Data was captured and analyzed using Chromeleon v6.8 software.

Figure 6:
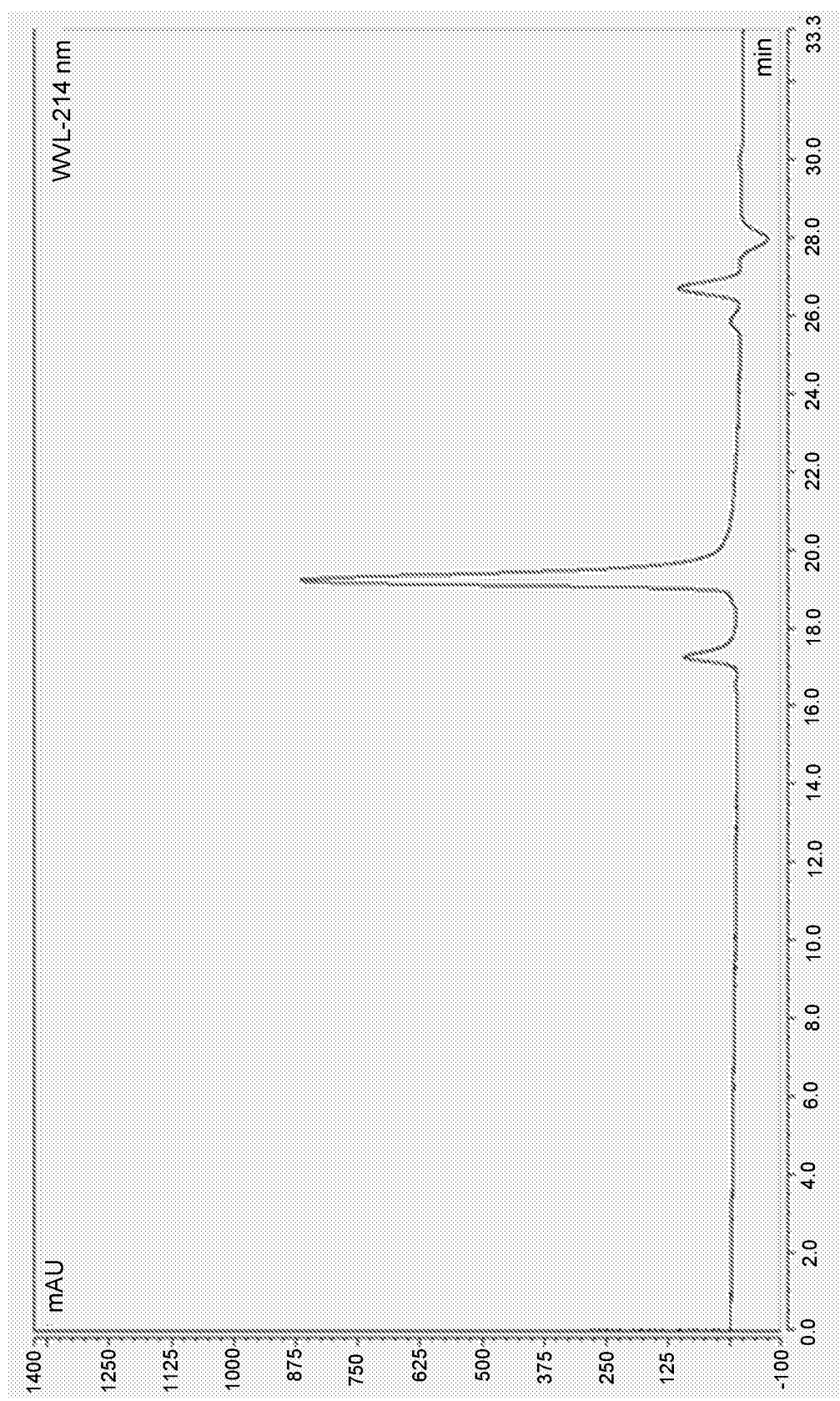
FIG. 6 illustrates the results of size exclusion high performance liquid chromatography on a formulation comprising purified CRM 197 in HEPES buffer which does not comprise any excipients that had been stored at −80 C for 1.3 years. Prior to heat treatment, the sample contained 10.48% dimers (at 17.25 minutes).

FIG. 6 demonstrates that the presence of dimers can be detected and quantified using sec-HPLC in a purified CRM 197 solution. The larger dimer elutes (17.25 minutes) prior to the elution of the smaller monomer (19.22 minutes) while small molecules and the solvent front are detected around 26 minutes. The area of the peak is proportional to the amount of material present.

Figure 7:
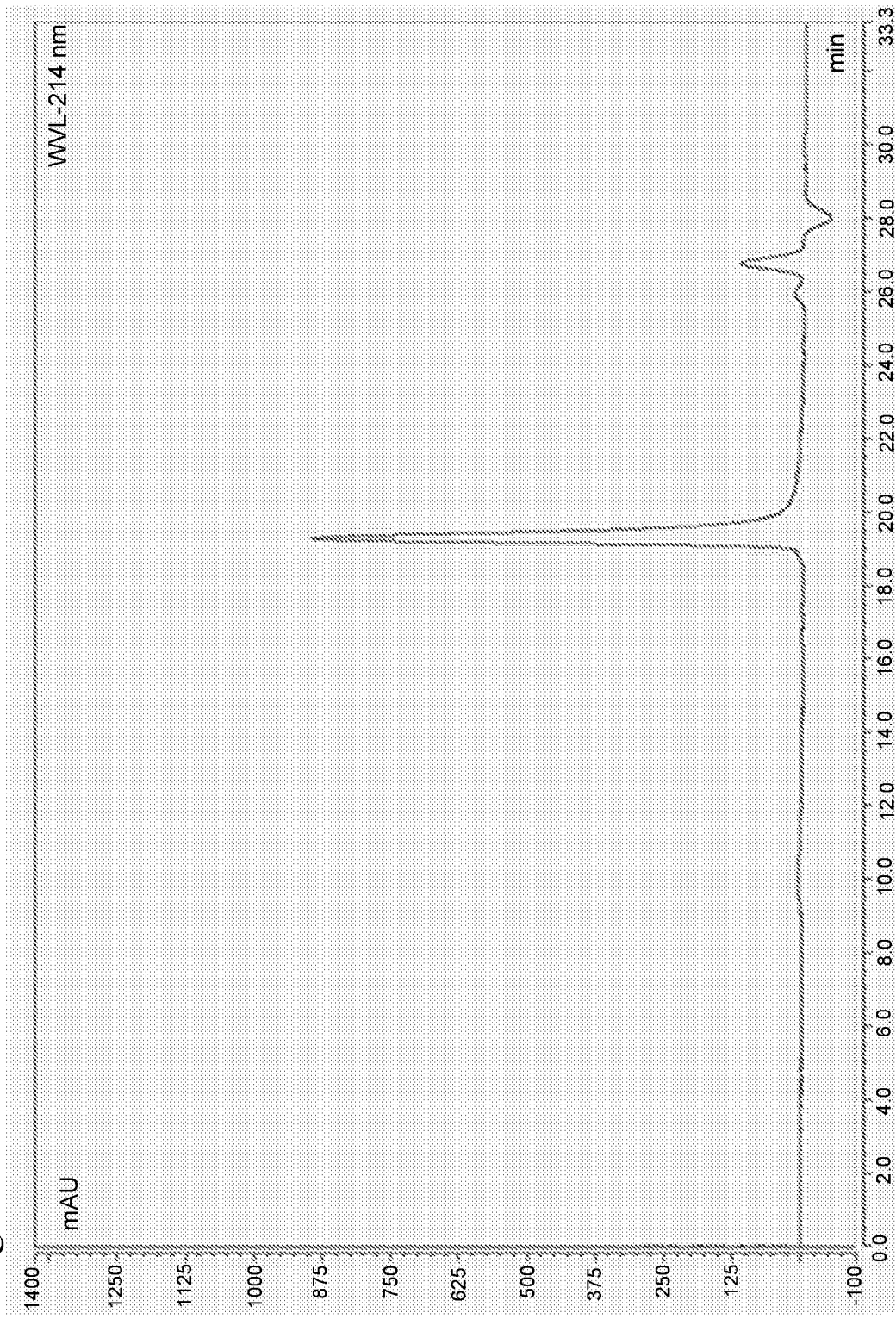
FIG. 7 illustrates the effect of a one hour heat treatment at 37° C. of the purified CRM 197 solution. CRM 197 dimers were entirely converted to monomer form.
Figure 8:
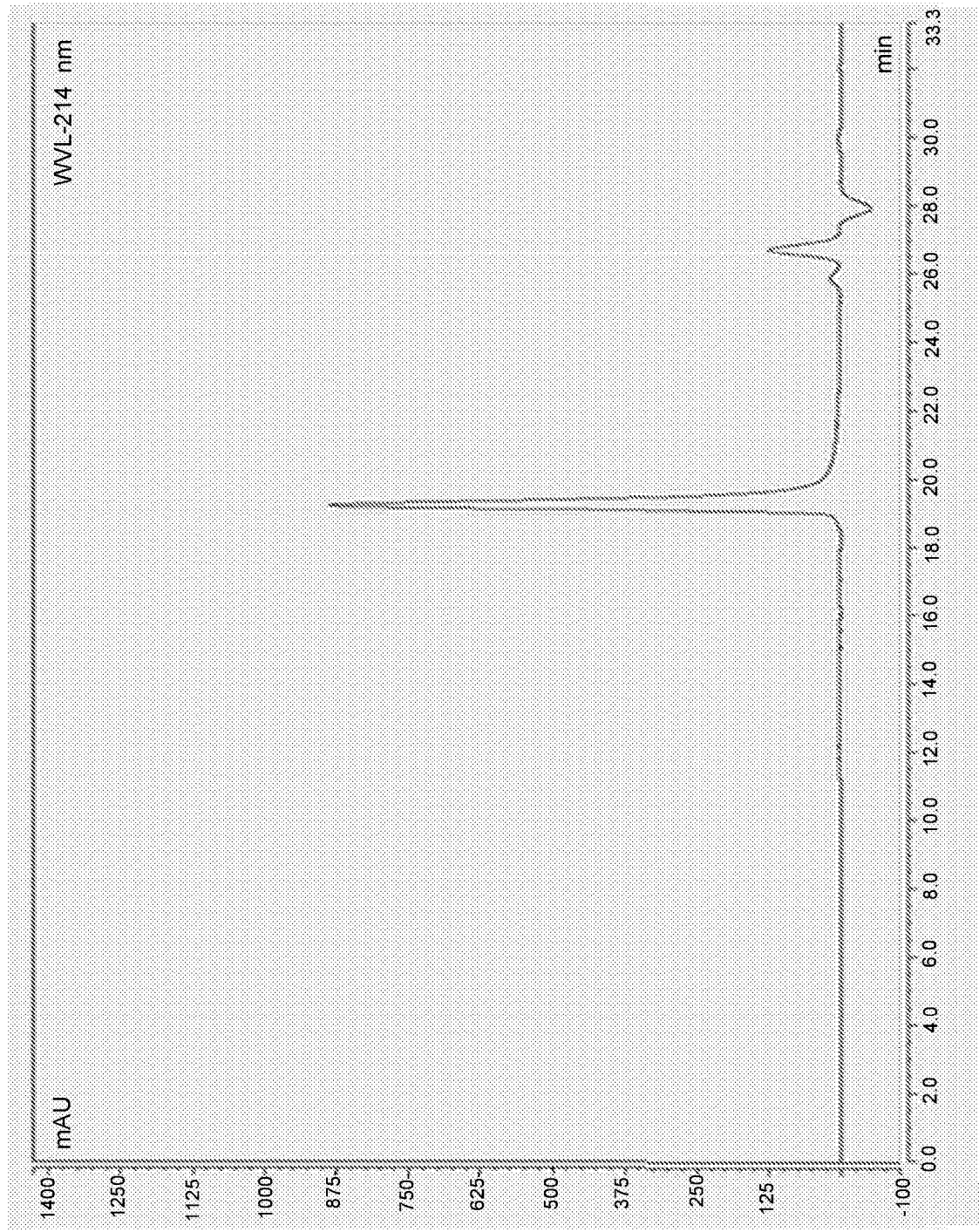
FIG. 8 illustrates the effect of a five hour heat treatment at 37° C. of the purified CRM 197 solution. No additional effects beyond that seen for the one hour heat treatment were observed and no degradation of CRM 197 was observed.

FIG. 7 demonstrates that incubation of the purified CRM 197 solution for one hour at 37 C removed all detectable traces of CRM 197 dimer. Incubation of purified CRM 197 solution for up to 5 hours at 37 C had no detectable change in quality as shown in FIG. 8.

The results are illustrated in table form below:

|  | Heat treatment | Protein State | Retention time, min | Area, relative units (214 nm) | Dimer/monomer, % |
|---|---|---|---|---|---|
| Sample 1 | 0 min | Dimer | 17.25 | 39.13 | 10.48% dimer |
|  |  | Monomer | 19.22 | 373.24 | 89.52% monomer |
| Sample 2 | 1 h × 37 C. | Monomer | 19.28 | 353.28 | 100% monomer |
| Sample 3 | 2 h × 37 C. | Monomer | 19.25 | 332.13 | 100% monomer |
| Sample 4 | 3 h × 37 C. | Monomer | 19.25 | 330.28 | 100% monomer |
| Sample 5 | 4 h × 37 C. | Monomer | 19.22 | 322.38 | 100% monomer |
| Sample 6 | 5 h × 37 C. | Monomer | 19.22 | 344.41 | 100% monomer |

These results demonstrate the long-term stability of CRM 197 in an aqueous HEPES formulation that does not comprise excipients. Briefly, CRM 197 was found to be stable in such a formulation for 1.3 years at −80° C., although some dimerization was detected. Accordingly, such a formulation should be thawed for at least one hour (and up to five hours) at 37° C. prior to conjugation in order to ensure that lysines are exposed. Although beneficial for protein stability, excipients can interfere with subsequent procedures and require removal. In the case of CRM197, the use of excipients containing carbonyl (aldehyde or carboxyl) groups can compete with the conjugation of the desired ligand if not completely removed. The removal of the excipient is usually achieved by diafiltration which can be a time consuming step.

What is claimed is:

1. A method for purifying CRM 197 obtained from a bacterial cell culture comprising: (i) contacting a bacterial cell lysate comprising CRM 197 or a fermentation medium comprising CRM 197, said lysate or medium further comprising a redox agent and optionally a solubilizing agent, with a mixed mode cation exchange media comprising a ligand comprising an aromatic group, substituted with a primary amine and a carboxylic acid group and equilibrated with buffer having a pH between 6.5 and 7.0 under conditions in which CRM 197 binds to the mixed mode cation exchange chromatography media and eluting CRM 197 to generate a first eluate comprising CRM 197; (ii) contacting the first eluate with an anion exchange chromatography media under conditions in which CRM 197 binds or does not bind to the anion exchange chromatography media and eluting CRM 197 to generate a second eluate comprising CRM 197; and (iii) contacting the second eluate with a hydroxyapatite chromatography media under conditions in which CRM 197 binds to the hydroxyapatite chromatography media and eluting CRM 197, wherein no additional chromatographic purifications steps occur between (i)-(iii).

2. The method of claim 1 wherein the bacterial cell lysate or fermentation medium is clarified by filtration and/or centrifugation, prior to contacting with the mixed mode cation exchange media.

3. The method of claim 1, wherein an eluate or flow-through comprising CRM 197 is subjected to diafiltration, dilution and/or buffer exchange prior to contacting with a subsequent chromatography media.

4. The method of claim 1, wherein the mixed mode ion exchange media is washed with buffer having a pH above 5.85 and a conductivity below about 11 mS/cm.

5. The method of claim 4, wherein the mixed mode ion exchange media is washed with buffer having a pH between 6.0 and 8.0 and a conductivity of about 10 mS/cm.

6. The method of claim 4, wherein the mixed mode ion exchange media is washed with buffer having a pH between 6.5 and 7.0.

7. The method of claim 1, wherein CRM 197 is eluted from the mixed mode ion exchange media with a buffer having a pH between 8.0 and 10.0.

8. The method of claim 1, wherein the mixed mode ion exchange media is CMM Hypercel (aminobenzoic acid).

9. The method of claim 1, wherein the hydroxyapatite chromatography media is equilibrated and/or washed with a buffer comprising about 0.5 mM to about 4 mM NaPO4, optionally comprising about 100 to 200 mM NaCl, at a pH of about 7.0 to about 8.0 and wherein CRM 197 is eluted from the hydroxyapatite chromatography media with at least one elution buffer comprising from about 1 mM to about 200 mM NaPO4 and from 100 to 200 mM NaCl at a pH of about 7.0 to about 8.0.

10. The method of claim 1, wherein the hydroxyapatite chromatography media is equilibrated and/or washed with a buffer having a pH from 7.0 to 9.0, and wherein CRM 197 is eluted with a gradient to 1 M sodium sulfate, 0.5 to 4 mM CaCL2 at a pH of 7.0 to 9.0.

11. The method of claim 1, wherein the anion exchanger in bind and elute mode is equilibrated and/or washed with a solution comprising 25 mM to 75 mM salt, at a pH of 7.0 to 9.0.

12. The method of claim 1, wherein CRM 197 is eluted from the anion exchanger in bind and elute mode with a linear salt gradient comprising a segment comprising about 200 mM to about 280 mM salt, at a pH of 7.0 to 9.0.

13. The method of claim 1, wherein the redox agent is selected from the group of disulfide containing compounds consisting of glutathione disulfide, cystine, cystamine, diphenyl disulfide, and lipoic acid or is selected from the group of non-disulfide containing compounds consisting of sodium iodate, 1,10 phenanthroline, $CuCl_2$, and $FeSO_4$.

14. The method of claim 1, wherein the mixed mode ion exchange media is equilibrated with buffer having a pH of about 6.75.

15. The method of claim 4, wherein the mixed mode ion exchange media is washed with buffer comprising about 100 mM NaCl, and/or about 20 mM arginine at a pH of about 6.75.

16. The method of claim 1, wherein the hydroxyapatite chromatography media is equilibrated and/or washed with a buffer comprising about 2 mM NaPO4, optionally comprising about 150 mM NaCl, at a pH of about 7.4 and wherein CRM 197 is eluted from the hydroxyapatite chromatography media with at least one elution buffer comprising from about 2 mM to about 150 mM NaPO4 and about 150 mM NaCl at a pH of about 7.4.

* * * * *